US006856913B1

(12) United States Patent
Silberstein

(10) Patent No.: US 6,856,913 B1
(45) Date of Patent: Feb. 15, 2005

(54) DECENTRALIZED PATIENT MANAGEMENT METHOD

(75) Inventor: Richard B. Silberstein, Blackburn (AU)

(73) Assignee: Swineburn Limited, Hawthorn (AU)

(*) Notice: Subject to any disclaimer, the term of this patent is extended or adjusted under 35 U.S.C. 154(b) by 0 days.

(21) Appl. No.: 09/700,296

(22) PCT Filed: May 14, 1999

(86) PCT No.: PCT/AU99/00365

§ 371 (c)(1),
(2), (4) Date: Jan. 19, 2001

(87) PCT Pub. No.: WO99/59469

PCT Pub. Date: Nov. 25, 1999

(30) Foreign Application Priority Data

May 15, 1998 (AU) ............................................. PP3547

(51) Int. Cl.⁷ ........................ G01N 33/48; A01N 37/18; A01N 43/04
(52) U.S. Cl. ............................... 702/19; 514/2; 514/44
(58) Field of Search ........................ 514/2, 44; 702/19; 703/11

(56) References Cited

U.S. PATENT DOCUMENTS

| | | | |
|---|---|---|---|
| 2,860,627 A | 11/1958 | Harden ........................ 128/731 |
| 3,087,487 A | 4/1963 | Clynes ........................ 128/731 |
| 3,498,287 A | 3/1970 | Ertl .............................. 128/731 |
| 3,513,834 A | 5/1970 | Suzuki et al. ................. 128/731 |
| 3,689,135 A | 9/1972 | Young et al. .................. 351/39 |
| 3,809,069 A | 5/1974 | Bennett ....................... 128/731 |
| 3,855,998 A | 12/1974 | Hidalgo-Briceno ..... 128/745 X |
| 3,880,144 A | 4/1975 | Coursin et al. .............. 128/2.1 |
| 3,892,227 A | 7/1975 | Coursin et al. .............. 128/2.1 |
| 3,901,215 A | 8/1975 | John ....................... 128/745 X |
| 3,998,213 A | 12/1976 | Price ........................... 128/644 |
| 4,083,365 A | 4/1978 | Yancey ....................... 128/731 |
| 4,094,307 A | 6/1978 | Young, Jr. .................. 128/731 |
| 4,140,997 A | 2/1979 | Brady ......................... 128/732 |
| 4,201,224 A | 5/1980 | John ........................... 128/731 |
| 4,216,781 A | 8/1980 | John ........................... 128/731 |
| 4,244,376 A | 1/1981 | Fisher et al. ................. 128/731 |
| 4,304,242 A | 12/1981 | Siarkiewicz et al. ........ 128/745 |
| 4,407,299 A | 10/1983 | Culver ........................ 128/731 |
| 4,421,122 A | 12/1983 | Duffy .......................... 128/731 |
| 4,462,411 A | 7/1984 | Rickards ..................... 128/731 |
| 4,493,327 A | 1/1985 | Bergelson et al. .......... 128/731 |
| 4,493,539 A | 1/1985 | Cannon, Jr. ................. 128/731 |
| 4,537,198 A | 8/1985 | Corbett ........................ 128/639 |
| 4,566,464 A | 1/1986 | Piccone et al. ............. 128/731 |
| 4,570,640 A | 2/1986 | Barsa .......................... 128/741 |
| 4,610,259 A | 9/1986 | Cohen et al. ................ 128/731 |
| 4,632,122 A | 12/1986 | Johansson et al. .......... 128/644 |
| 4,632,126 A | 12/1986 | Aguilar ....................... 128/732 |
| 4,649,482 A | 3/1987 | Raviv et al. ................. 128/731 |
| 4,665,499 A | 5/1987 | Zacharski et al. .......... 128/731 |
| 4,676,611 A | 6/1987 | Nelson et al. ............... 128/731 |
| 4,744,029 A | 5/1988 | Raviv et al. ............. 128/731 X |
| 4,794,533 A | 12/1988 | Cohen ..................... 128/731 X |
| 4,832,480 A | 5/1989 | Kornacker et al. ......... 128/731 |
| 4,861,154 A | 8/1989 | Sherwin et al. ............. 128/731 |
| 4,862,359 A | 8/1989 | Trivedi et al. ......... 364/413.05 |
| 4,869,264 A | 9/1989 | Silberstein ................... 128/731 |
| 4,878,498 A | 11/1989 | Abrams et al. ............. 128/731 |
| 4,892,106 A | 1/1990 | Gleeson, III ................ 128/745 |
| 4,913,160 A | 4/1990 | John .......................... 128/731 |
| 4,932,416 A | 6/1990 | Rosenfeld ................... 128/731 |
| 4,955,388 A | 9/1990 | Silberstein .................. 128/731 |
| 4,955,938 A | * 9/1990 | Romer et al. ............... 102/430 |
| 4,974,602 A | 12/1990 | Abraham-Fuchs et al. .. 128/731 |
| 4,977,896 A | 12/1990 | Robinson et al. ....... 128/653 R |
| 5,331,969 A | 7/1994 | Silberstein .................. 128/731 |
| 5,357,427 A | 10/1994 | Langen et al. .............. 364/413 |
| 5,730,146 A | 3/1998 | Itil et al. ..................... 128/732 |
| 6,035,230 A | * 3/2000 | Kang et al. ................. 600/509 |
| 6,052,619 A | * 4/2000 | John .......................... 600/544 |

FOREIGN PATENT DOCUMENTS

| | | |
|---|---|---|
| FR | 2604889 | 4/1988 |
| WO | WO 87 00745 | 2/1987 |

OTHER PUBLICATIONS

"Visual Evoked Response Phase Spectrum as Measure of Latency," J.H. Strickland, Jr., et al., 1985 IEEE, pp. 128–134.

"Monitoring the Level of Anesthesia by Automatic Analysis of Spontaneous EEG Activity," McEwen et al., IEEE Transactions on Biomedical Engineering, Jul. 1975, pp. 299–305.

A. Papanicolauo et al., "Prove Evoked Potentials: Theory, Method and Applications," Intern. J. Neuroscience, vol. 24, pp. 107–131 (1984).

Proceedings of the Eleventh Annual Northeast Bioengineering Conference, Mar. 14, 15, 1985, Worcester Polytechnic Institute, Worcester, Massachusetts, Walter S. Kuklinski and William J. Ohley, pp. 128–134.

Descriptive Linear Modeling of Steady–State Visual Evoked Response by William H. Levinson, Andrew M. Junker and Kevin Kenner, Proceedings of the Twenty–First Annual Conference on Manual Control. Jun. 17–19, 1985, Ohio State University, Columbus Ohio, pp. 1.1–1.16.

(List continued on next page.)

*Primary Examiner*—Ardin H. Marschel
(74) *Attorney, Agent, or Firm*—Wolf, Greenfield & Sacks, P.C.

(57) ABSTRACT

A system (2) for evaluating the efficiency of therapeutic treatments of patients (40) located at remote sites (6) by communicating a cognitive task to the remote site via a network (10) which provides two-way communication between a central analysis site and the remote sites, presenting the task to the patient before, during, or after carrying out a therapeutic intervention or treatment, detecting brain response from the patient, and communicating this response to the central analysis site via the network.

13 Claims, 12 Drawing Sheets

OTHER PUBLICATIONS

J. Ciociari et al., "The Multichannel Electrode Helmet," Proceedings Conference on Engineering And Physical Sciences In Medicine, Melbourne, p. 52 (1987) (Abstract only).

J. Dubinsky et al., "A Simple Dot–Density Topogram For EEG," Electroenceph. Clin. Neurophysical., vol. 48, pp. 473–477 (1980).

R. Galambos et al., "Dynamic Changes In Steady–State Responses," In E. Basar (Ed) Springer Series In Brain Dynamics, I. Springer–Verlag, Berlin Heidelberg, pp. 103–122 (1988).

J. Johnstone et al., "Regional Brain Activity In Dyslexic And Control Children During Reading Tasks: Visual Probe Event– Related Potentials," Brain and Language, vol. 21, p. 233–254 (1984).

A. Junker et al., "The Effect of Task Difficulty On The Steady State Visual Evoked Response." 1986 IEEE. Pp. 905–908.

W. R. Klemm et al., "Hemispheric Lateralization And Handedness Correlation Of Human Evoked 'Steady–State' Responses To Patterned Visual Stimuli." Physiological Psychology, vol. 8. pp. 409–416 (1980).

D. Regan, "Steady–State Evoked Potentials," Journal of the Optical Society of America, vol. 67. Pp. 1475–1489 (1977).

M. A. Schier et al., "Requirements of a High Spatial Resolution Brain Electrical Activity Data Acquistion System." Neuroscience Letters, Suppl. 30. P. S151 (1988) (Abstract only).

R. B. Silberstein et al., "Topographic Distribution of the Steady State Visually Evoked Potential," Neuroscience Letters, Suppl. 30. p. S123 (1988) (Abstract only).

P. S. Sebel et al., "Evoked Responses—A Neurophysiological Indicator of Depth of Anasthesia?". British Journal of Anaesthesia. Vol. 57, No. 9, pp. 841–842 (Sep. 1985).

G. F. Wilson et al., Steady State Evoked Responses: Correlations With Human Cognition: Psychophysiology, vol. 23, p. 57 (1986) (Abstract only).

* cited by examiner

DECENTRALIZED PATIENT MANAGEMENT METHOD

This application is a 371 filing of PCT/AU99/00365, filed May 14, 1999.

The present invention relates to a decentralised patient management system. The invention also relates to a method of evaluating the efficacy of therapeutic intervention in a patient by assessment of different steady state visually evoked potentials.

U.S. Pat. Nos. 4,955,388 and 5,331,969 (the contents of which are hereby incorporated herein by reference) disclose techniques for obtaining a steady state visually evoked potential (SSVEP) from a patient. These patents disclose the use of Fourier analysis in order to rapidly obtain the SSVEP's and changes thereto. It has now been appreciated that those techniques can be utilised to monitor the efficacy of treatment of patients. In one embodiment patients are located at one or more remote sites and the SSVEP signals are sent to a central analysis site for processing. The central analysis site reports back to the remote site where the medical practitioner, psychiatrist or the like can receive a report on the likely suitability of a particular treatment for the patient. By using standard communications techniques and the Internet the remote sites can be established with relatively inexpensive hardware and software, but have access to the more sophisticated analysis system located at the central analysis site.

In another embodiment, the efficacy of a therapeutic intervention or treatment can be made by assessing the differences between SSVEP's of a patient before and during the application of a treatment or intervention.

According to the present invention there is provided a system for evaluating the efficacy of therapeutic treatments of patients located at remote sites, the system including:

a central analysis site;

a plurality of remote test sites;

input means at the central analysis site for inputting signals representative of a cognitive task;

means for communicating the input signals to selected remote test sites via a network which provides two-way communication between the central analysis site and the remote sites;

receiving means at the remote test sites for receiving the input signals and presenting the cognitive task to a patient (i) before and (ii) during or after carrying out a therapeutic intervention or treatment;

detecting means at the remote test sites for detecting brain response signals from the patient to said cognitive tasks;

means for communicating said brain response signals to said central analysis site via the network; and processing means for assessing the efficacy of the therapeutic intervention or treatment on the basis of differences in brain response signals before and during or after carrying out the therapeutic intervention or treatment.

The invention also provides a method of evaluating the efficacy of therapeutic intervention in a patient including the steps of recording a first steady state visually evoked potential (SSVEP) from the patient while undertaking a first cognitive task, carrying out a therapeutic intervention or treatment on the patient, recording a second steady state visually evoked potential (SSVEP) from the patient while undergoing a second cognitive task, assessing the efficacy of the therapeutic intervention on the basis of differences between the first and second SSVEP's.

Preferably the first and second cognitive tasks are similar or the same.

Preferably the therapeutic intervention or treatment is for the purpose of treating neuropsychiatric disorders.

Preferably the step of carrying out the therapeutic intervention includes the step of administering a test dose of a psychotropic medication.

The psychotropic medication may comprise all chemical compounds or combination of chemical compounds used in the treatment of psychiatric, psychological, behavioural, educational or neurological disorders.

Preferably the step of assessing the efficacy includes the steps of detecting changes associated with therapeutic intervention in the SSVEP amplitude and/or phase topography and/or inter-electrode SSVEP coherence.

The invention also provides a method of evaluating the efficacy of therapeutic treatments of patients located at remote sites, the method including the steps of:

causing a patient to carry out a first cognitive task at a remote site;

obtaining first signals representing the response of the patient's brain to said cognitive task;

carrying out a therapeutic treatment on the patient;

obtaining second signals representing the response of the patient's brain to a second cognitive task whilst under the influence of said treatment;

transmitting the first signals and the second signals to a central analysis site;

analysing the first and second signals at the central analysis site to assess the efficacy of the therapeutic treatment; and transmitting the results of the assessment to the remote site.

Preferably the first and second signals are steady state visually evoked potentials (SSVEP's).

The invention also provides a system for evaluating the efficacy of therapeutic treatments of patients located at remote sites, the system including:

a central analysis site:

input means for inputting signals representative of a cognitive task;

means for communicating the input signals to selected remote test sites via a network which provides two-way communication between the central analysis site and the remote sites for transmission of said signals to selected remote sites for presentation to a patient (i) before and (ii) during or after carrying out a therapeutic intervention or treatment;

means for receiving said brain response signals of the patients transmitted to said central analysis site via the network; and processing means for assessing the efficacy of the therapeutic intervention or treatment on the basis of differences in brain response signals before and during or after carrying out the therapeutic intervention or treatment.

The invention also provides a method of evaluating the efficacy of therapeutic intervention in a patient including the steps of:

obtaining data representing a first steady state visually evoked potential (SSVEP) from a patient at a remote site while undertaking a first cognitive task;

obtaining data representing a second steady state visually evoked potential (SSVEP) from the patient while undergoing a second cognitive task during or after a therapeutic intervention; and assessing the efficacy of the therapeutic intervention on the basis of differences between the first and second SSVEP's.

The invention also provides a test site for evaluation of the efficacy of a therapeutic treatment of a patient, the test site including:

receiving means for receiving input signals via a network from a central analysis site, said signals being representative of cognitive tasks;

presenting means for presenting the cognitive task to the patient (i) before and (ii) during or after carrying out a therapeutic intervention or treatment;

detecting means for detecting brain response signals from the patient to said cognitive tasks; and means for communicating said brain response signals obtained before and during or after carrying out a therapeutic intervention or treatment to said central analysis site via the network.

The invention also provides a method of evaluating the efficacy of therapeutic treatments of a patient located at a test site, the method including the steps of:

causing a patient to carry out a first cognitive task at the test site;

obtaining first signals representing the response of the patient's brain to said cognitive task;

carrying out a therapeutic intervention or treatment on the patient;

obtaining second signals representing the response of the patient's brain to a second cognitive task whilst under the influence of said treatment;

transmitting the first signals and the second signals to a central analysis site via a network wherein the first and second signals are analysed to assess the efficacy of the therapeutic treatment; and receiving at the test site output signals from the central analysis site which demonstrate the efficacy of the therapeutic intervention or treatment on the patient.

The invention will now be further described with reference to the accompanying drawings, in which.

Figure 1:
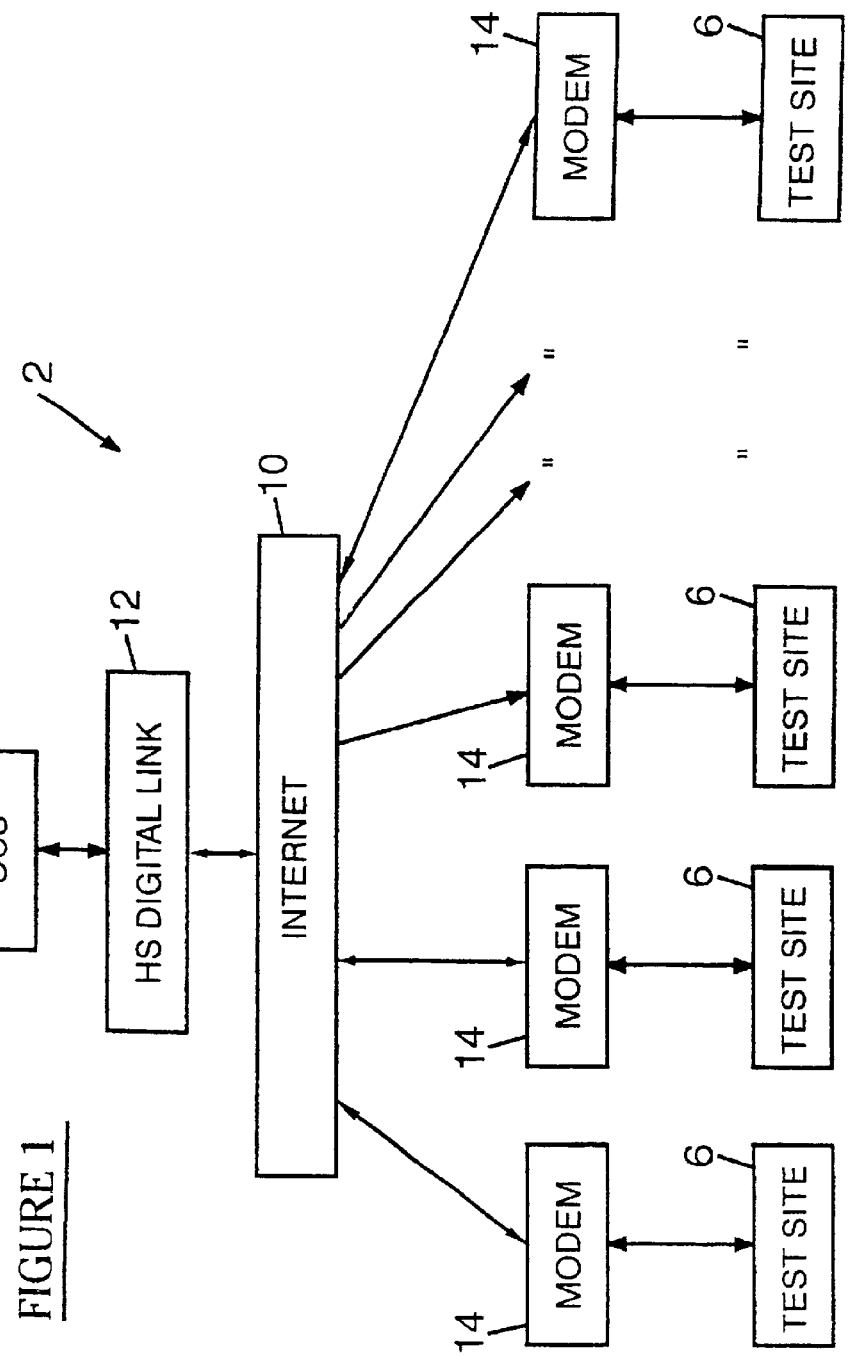
FIG. 1 is a block diagram of a decentralised patient management system of the invention.

FIG. 1 diagrammatically shows a decentralised patient management system 2 of the invention. It comprises a central analysis site 4 coupled to a plurality of remote test sites 6 by means of a network 8. The network 8 preferably comprises the Internet 10. The central analysis site 4 is coupled to the Internet by means of a high speed digital link 12 and each of the test sites 6 is connected to the Internet 10 by a modem 14 in the usual way.

Figure 2:
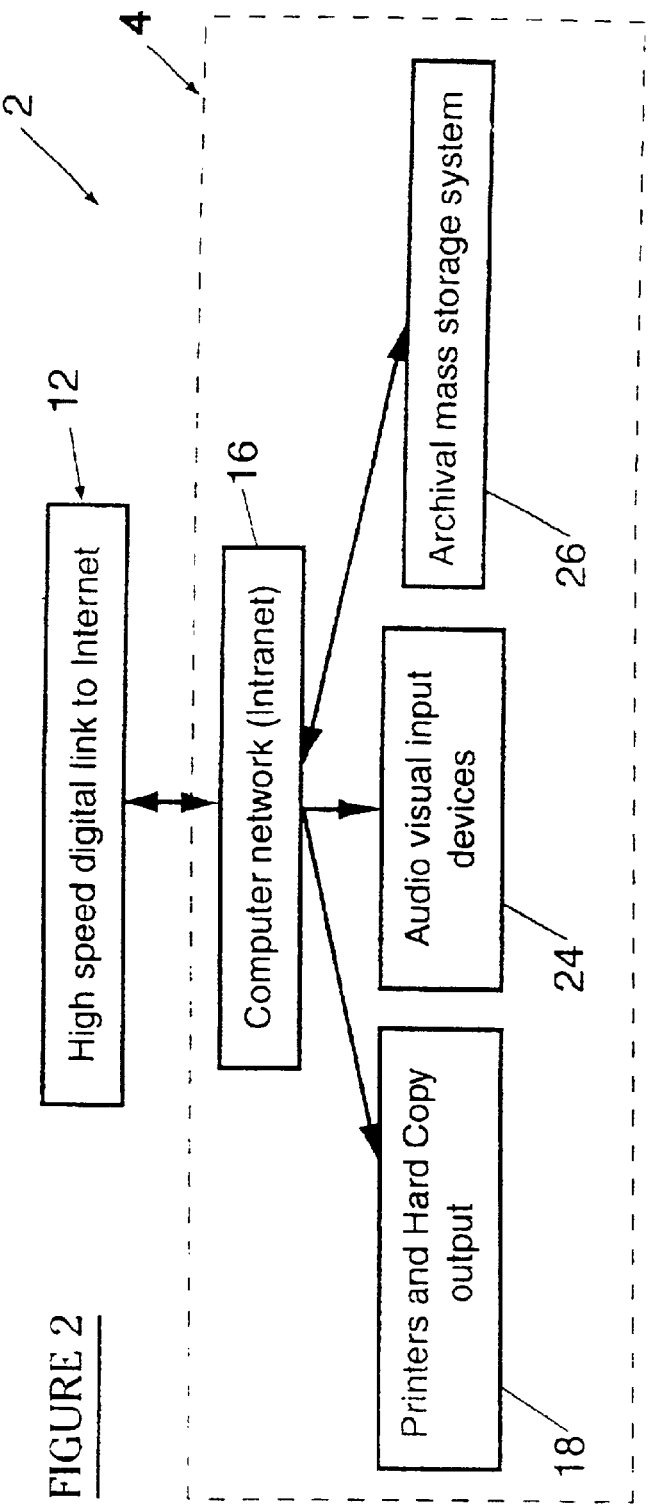
FIG. 2 is a block diagram of a central analysis site.

The central analysis site 4 is shown in more detail in FIG. 2. It comprises a central computer network 16 which is coupled for two-way communication to the link 12. The network 16 preferably comprises an array of computers which are linked together to achieve the computing power necessary to process multimedia material as well as analysing the large amount of EEG data from patents at the remote sites. Additionally, the network includes appropriate hardware and software to handle various forms of the cognitive tasks to be presented to patients. The cognitive tasks are selected to probe various aspects of brain function such as attention, recognition memory, working memory, cognitive flexibility, perceptual-motor function, the perception of emotion and the experience of emotion.

The network 16 is coupled to output devices 18 such as printers and/or video recorders or the like. The network 16 may be coupled to a number of input devices 24 such as video and/or audio input devices for receiving material to be presented to patients. The computer network 16 may be coupled to an archival mass storage system 26 for electronic storage of inputs and signals received from the remote sites. The central analysis site may include various output devices 28 including a printer, video recorder for producing video output.

The computer network 16 includes programs which utilise Fourier analysis to produce the changes in steady state response of the brain of a patient when the time varying cognitive task stimulus is presented to the patient. These techniques are disclosed in the aforementioned United States patents and therefore need not be described in detail. Alternatively, analog or hybrid circuitry may be provided at the central analysis site for detection of the required signals, again in accordance with the principles disclosed in the aforementioned patents.

In summary, the central analysis site 4 performs a number of functions including:

(i) receiving material to be presented to patients, (ii) producing digital cognited tasks which may be in the form of multimedia test material, (iii) downloading test sequences to specific patients, (iv) uploading brain electrical activity information from patients, (v) verifying patient state and quality of data, (vi) analysing brain activity, and (vii) producing reports in written and/or graphical form.

The remote sites 6 would normally be an appropriate medical establishment such as a hospital, clinic, psychiatrist's room or general practitioner's room. The electrical brain activity of the patient is recorded at the site and signals representative of this activity together with appropriate information on the cognitive task will be transferred to a central analysis site 4 via the Internet (or some other appropriate medium). The central analysis site 4 analyses the brain electrical activity and generates topographic maps of SSVEP amplitude and phase.

A typical session may involve testing a prospective patient's response to an anxiolytic (anxiety reducing) agent. The patient will undertake a cognitive task and steady state probe topography (SSPT) recording prior to and a predetermined time, say two hours, after the administration of a test does of the proposed medication. Brain activity before and after drug administration are compared and the clinician is advised from reports from the central analysis site 4 as to whether the patient is likely to benefit from long term administration of the medication and the possibility of side-effects.

Patient progress may also be monitored during a course of the drug with the SSPT methodology and decisions on variations in dosage levels as well as discontinuation of treatment may be made more efficiently.

A typical medical consultation utilising the system of the invention typically includes the following steps:

1. A patient consults a psychiatrist, clinical psychologist or other medical practitioner at the local site 6 about, say, a mood disorder or possible depression.
2. The medical practitioner establishes a preliminary diagnosis of depression and wishes to ascertain the most effective drug treatment.
3. The patient is asked to move to the recording site in a test room at the local site 6 where he or she is fitted with a multi-electrode helmet 38 or another multi-electrode system such as Electro-cap (ECI Inc., Eaton, Ohio, USA) as described below. The fitting is done by either a nurse or a technician. The helmet 38 or multi-electrode system is connected to a data acquisition system and computer as described in more detail below.
4. The nurse or technician logs onto the central analysis site 4 via the Internet and down-loads software for the relevant cognitive activation task. Preferably, the down-load is automatic and controlled by the central analysis site 4. Preferably the nurse or technician need only stipulate the type of psychiatric disorder under consideration.
5. The patient undertakes the cognitive activation task while SSPT recording takes place.
6. Brain electrical activity together with timing information on the cognitive task and the visual stimulus is encrypted and transmitted to the central analysis site 4.
7. Animated maps of the SSVEP amplitude and phase are generated at the central analysis site 4.
8. The patient is given a test dose of the selected medication and waits until plasma or brain levels have peaked. This is typically a period of from 1 to 2 hours.
9. Steps 5, 6 and 7 are then repeated.
10. Software at the central analysis site 4 analyses the SSVEP data and determines the differences between the first and second recording sessions. These differences are presented as animated brain maps and down-loaded to the remote site 6. In addition, a report may be generated which evaluates the likely long term patient response to the test medication.
11. The clinician considers the graphical data available along with the report and decides whether to test another agent or not. Testing of another agent would need to take place after the original test medication had been cleared from the body.

A similar approach could be used for ongoing monitoring of patient treatment.

The central analysis site 4 may utilise communication software and appropriate communications hardware to receive data from the remote sites 6 such as packages which are commercially available and therefore need not be described in detail. An example would be WS FTP32 or Cute FTP.

Brain electrical activity together with specific timing information on events in the test material is uploaded from the various test sites 6 as explained in more detail below.

Figure 3A:
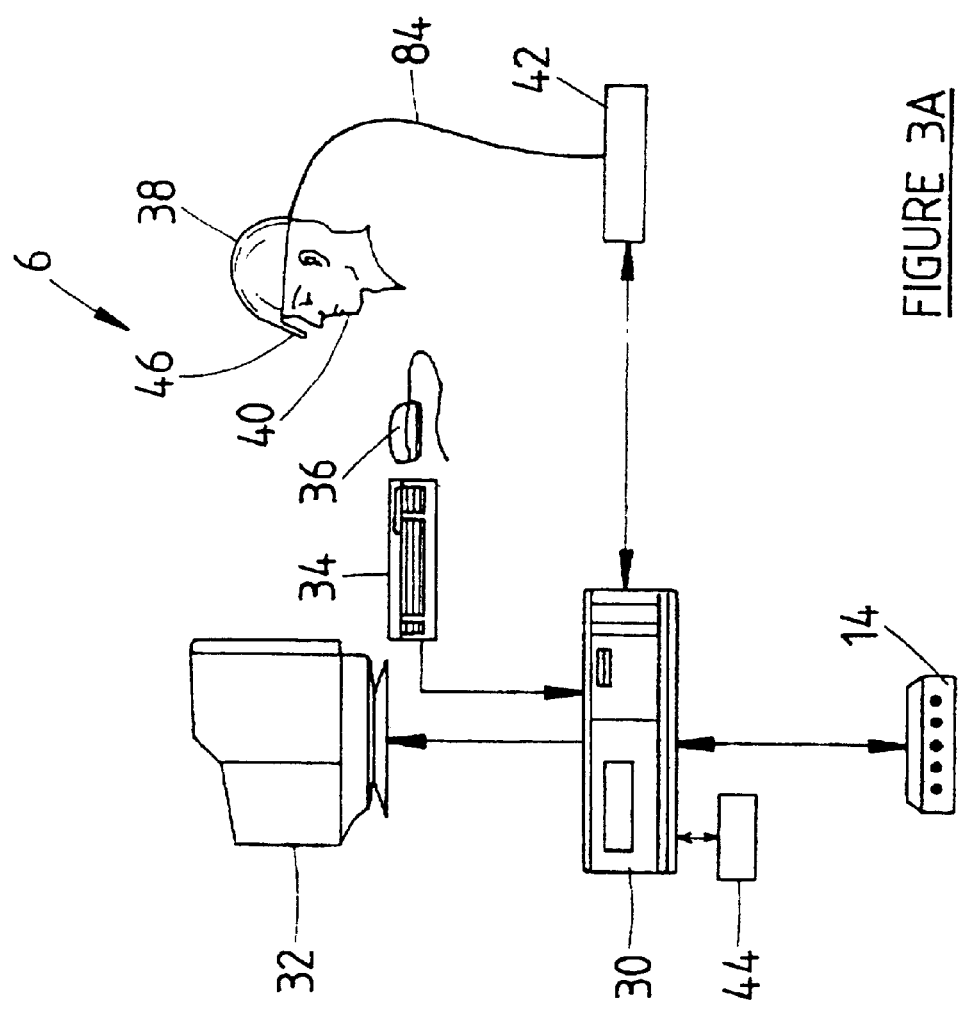
FIG. 3 is a block diagram for a remote site.
Figure 3B:
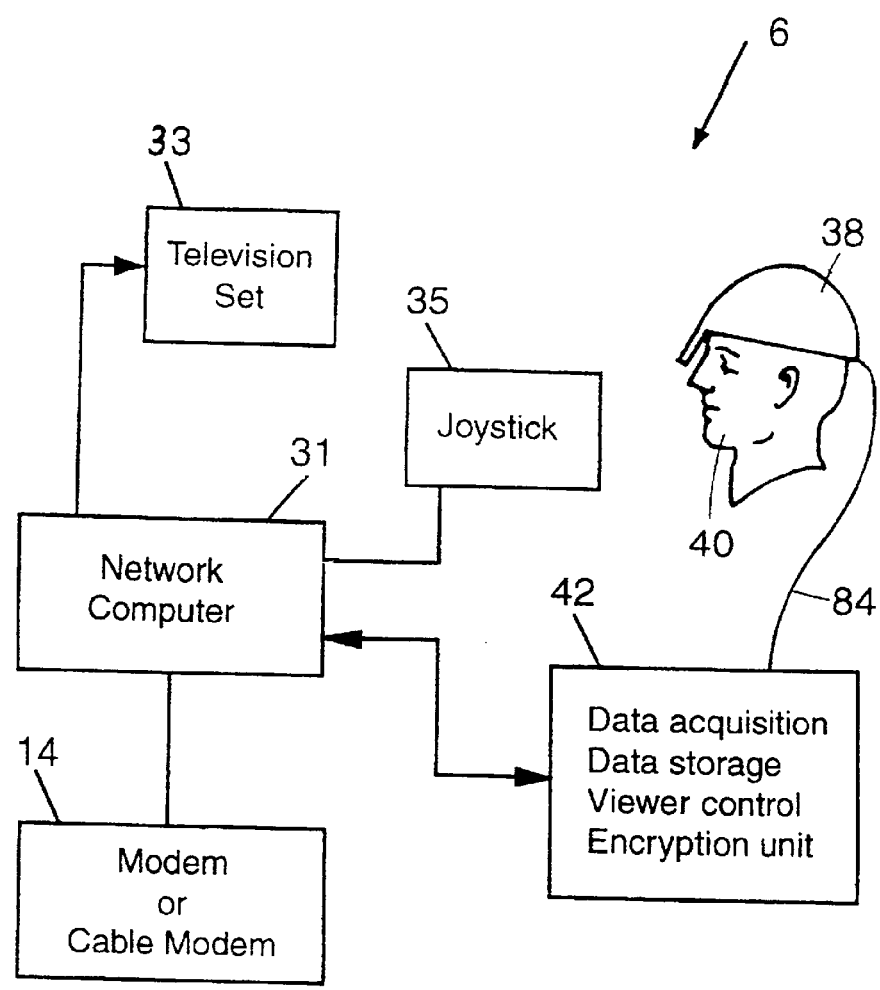

A typical test site 6 is shown in more detail in FIG. 3. The test site 6 typically includes a computer 30 coupled to a monitor 32 or television set, keyboard 34 and mouse 36 or other pointing device. The computer 30 is coupled to the Internet 10 by means of the modem 14, as shown. The test site 6 includes the helmet 38 or other multi-electrode system which is arranged to pickup electrical brain activity of the patient 40, the helmet or other multi-electrode system being coupled to the computer 30 by means of a control and interface circuit 42.

The computer 30 preferably comprises a network computer or PC or the like which includes an additional, dedicated hard drive 44 which is used exclusively for the invention. The software required for display of test material to the patient 40 and for controlling transmission of brain activity signals to the central analysis site 4 is preferably stored on the dedicated hard drive 44.

The helmet 38 includes a plurality of electrodes which can pickup brain activity of the patient 40. The helmet 38 includes a visor 46 through which the patient 40 can view the test material displayed on the monitor 32. The visor 46, however, provides for the display of a continuous-background flicker to the peripheral vision of the patient.

Signals representing electrical brain activity are detected by and recorded in the interface circuit 42. Generally speaking, the interface circuit 42 is arranged to filter and amplify the signals and then digitise and store the signals in an encrypted format.

Figure 5:
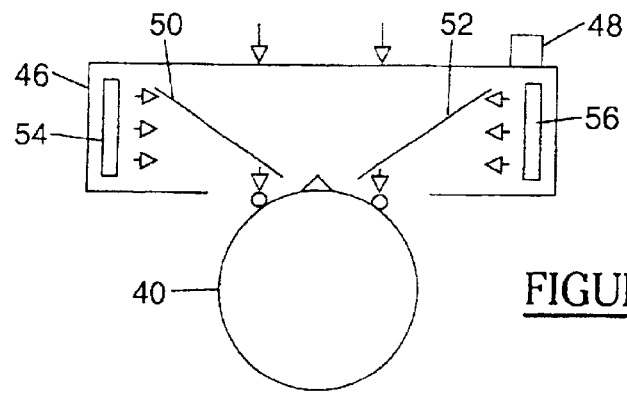
FIG. 5 is a schematic plan view showing input of signals to the eyes of a patient.
Figure 6:
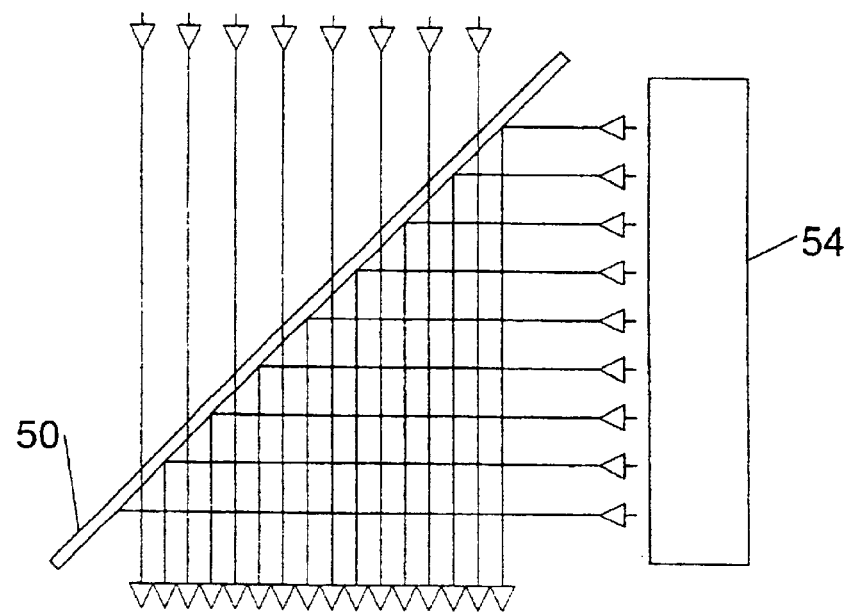
FIG. 6 shows the use of a partial mirror to combine signals to the eye of a patient.
Figure 7:
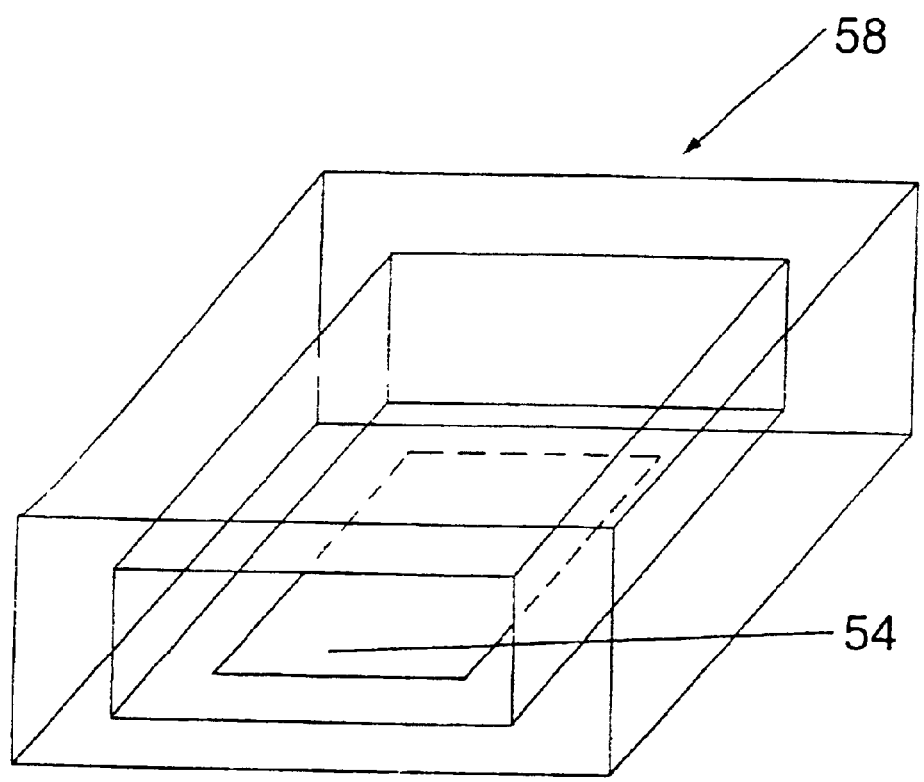
FIGS. 7, 8 and 9 are schematic views of LED shielding cages.
Figures 8, 9:
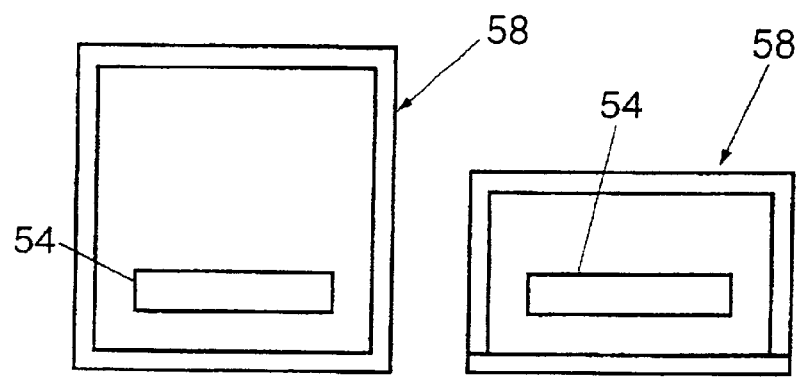
Figure 10:
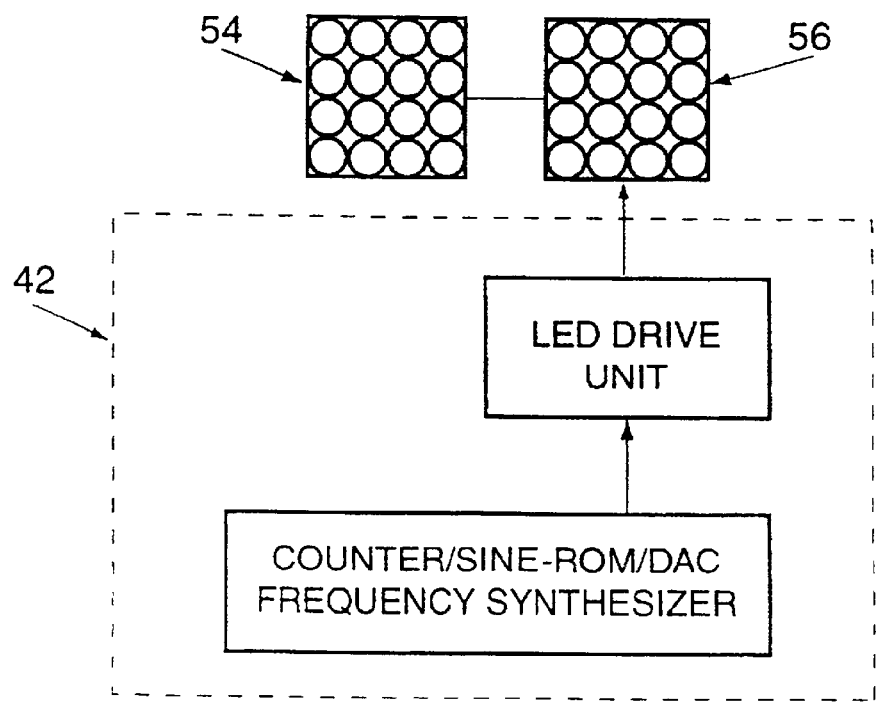
FIG. 10 is a schematic block diagram of part of the hardware at a remote site.

FIG. 5 schematically illustrates the optical components of the visor 46. The visor 46 includes two half-silvered mirrors 50 and 52 which enable the patient 40 to view the monitor 32 and also to receive the controlled background flicker. The background flicker is generated by means of first and second LED arrays 54 and 56 and is reflected towards the eyes of the patient through the mirrors 50 and 52. Each LED array preferably comprises nine LED devices arranged in a three by three array and located in a double Faraday cage 58 for electrical shielding. A typical Faraday cage 58 is schematically illustrated in FIGS. 7, 8 and 9.

Figure 4:
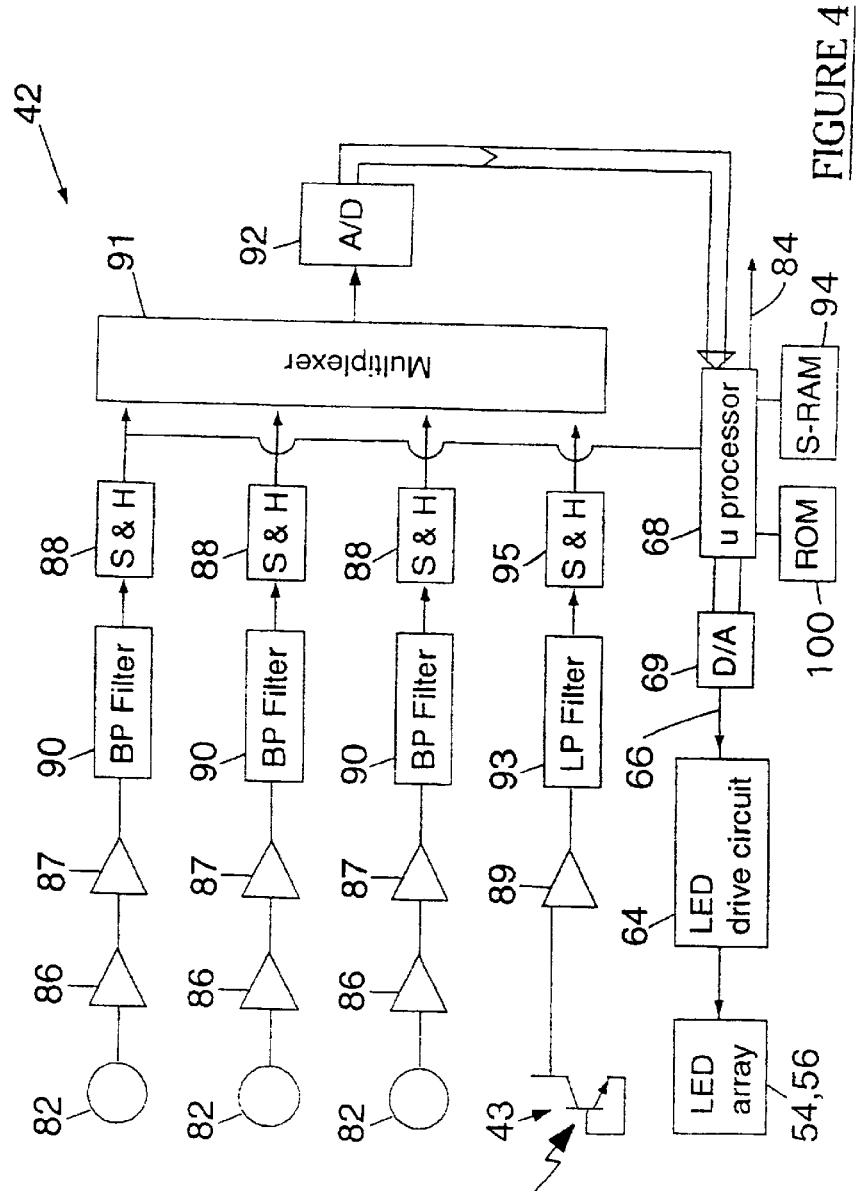
FIG. 4 is a schematic block diagram for part of the hardware at a remote site.
Figure 11:
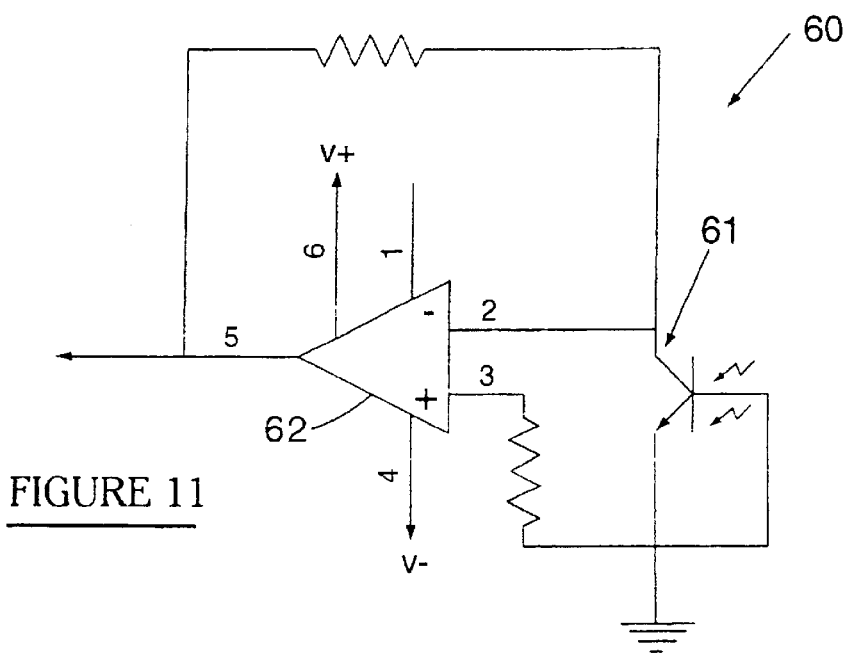
FIG. 11 shows part of an LED drive circuit.
Figure 13:
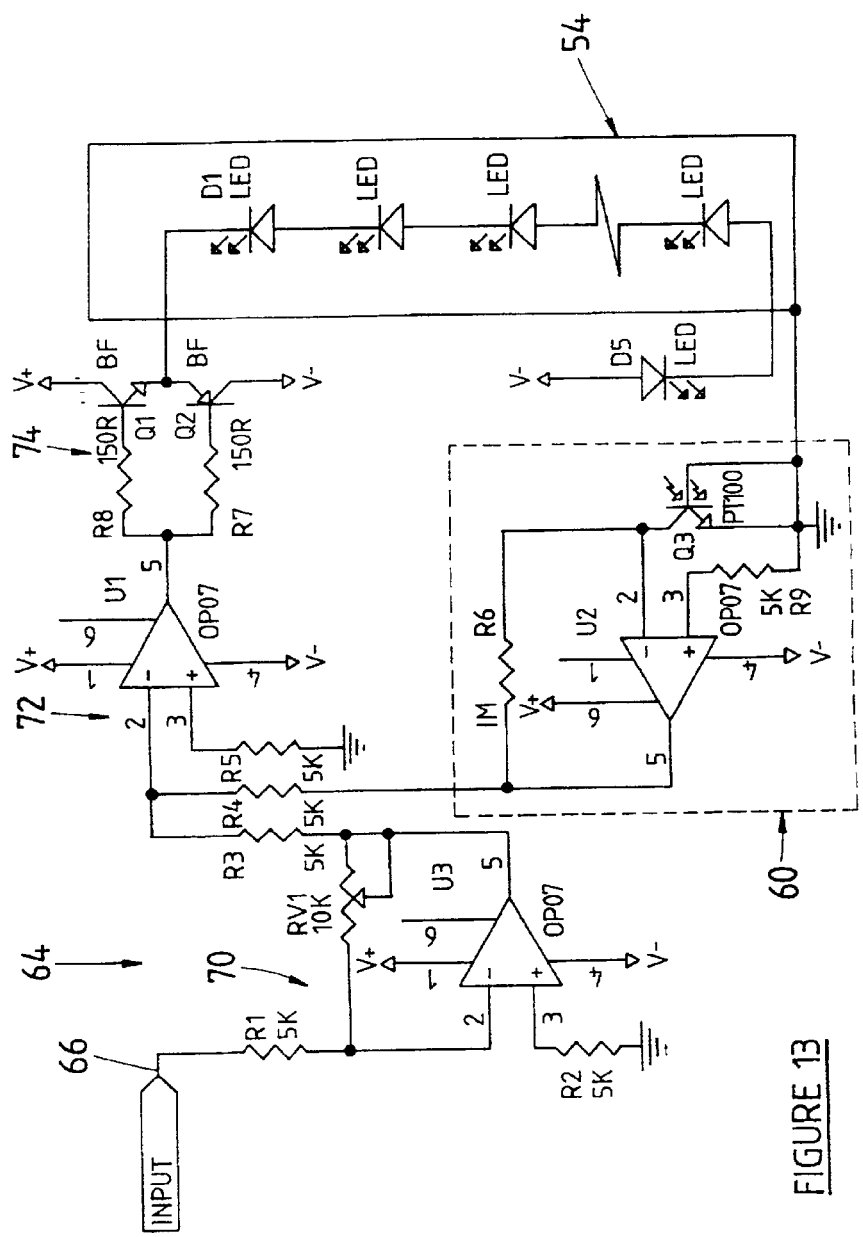
FIG. 13 shows in more detail circuitry for driving the LED array.
Figure 14:
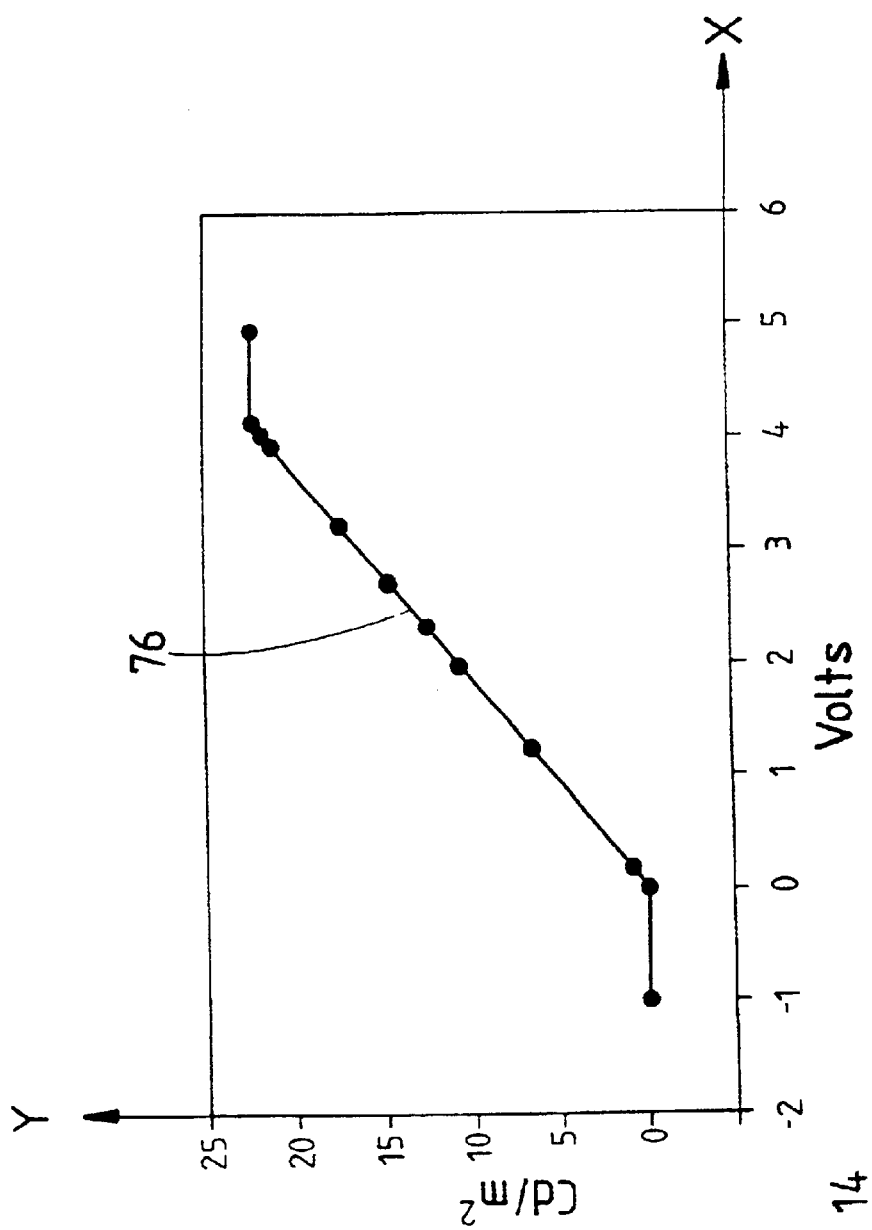
FIG. 14 shows the LED array luminance as a function of input voltage.

The luminance output of LED devices is not linear with respect to the applied voltage. Accordingly, in accordance with the invention, circuitry is provided to control the LED outputs so as to be linear. This is accomplished by using a feedback circuit 60 as shown in FIG. 11. The circuit 60 includes a phototransistor 61 coupled to the negative input of an operational amplifier 62. The phototransistor 61 is arranged to receive output from one or other of the LED arrays 54 and 56 or a further LED device connected thereto. The circuit 60 provides feedback for an LED drive circuit 64, as shown in FIG. 4. One circuit realisation for the LED drive circuit 64 is shown in FIG. 13. The drive circuit 64 includes an input 66 which receives input signals from a microprocessor controller 68 via a digital to analog converter 69. The input signals are amplified in amplifier stages 70, 72 and 74, the feedback circuit 60 provides negative feedback for the stages 72 and 74, as shown. The LED drive circuit 64 thus is able to produce a linear luminance output from the LED arrays 54 and 56, over a reasonable range of voltages applied to the input 66. This is graphically illustrated in FIG. 14 where the X-axis represents input voltage on the input 66 and the Y-axis represents luminance from the array 54 or 56. As indicated, the output luminance line 76 is substantially linear from about 0 volts to about 4 volts. Preferably, the LED flicker signals have a sinusoidal waveform.

The digital to analog converter 69 will produce the sinusoidal waveform when the microprocessor controller 68 sends the sine wave data held in a sine look-up table LUT stored in read only memory 100. A software counter will be used as a pointer to the sine wave LUT used to construct the sine wave. The output frequency of the waveform generator will be equal to the interrupting clock frequency divided by the number of digitised points 256 in the sine wave LUT incorporated in the program. The total harmonic distortion for a 256 point sine wave will be 0.71%. The reconstructed sine waves are then low-pass filtered by a suitable filter circuit provided in the LED drive circuit 64 to reduce the quantisation in the digitised waveforms and so reduce the total harmonic distortion.

The helmet 38 may be similar in appearance to a bicycle helmet and is used to house electrodes 82 for sensing brain electrical activity (EEG) and preferably has a single cable 84 connected to the rear of the helmet and extends to the circuit 42. The electrodes 82 are buffered by very high impedance unity gain amplifiers 86, as shown in FIG. 4. The electrodes are located at predetermined positions in the helmet or other multi-electrode system.

Each of the amplifiers 86 provides a unity gain (non-inverting) with very low input bias current (1 nA), very low noise (0.23 uV) and additional gain is provided by very high input impedance (400 Gohm) amplifiers 87. Electrode impedance may be estimated by injecting a very small current at the electrode site through a large resistance. The electrode impedance can then be estimated as it will form one arm of a potential divider. The outputs from the amplifiers 86 are coupled to sample and hold circuits 88 via filter circuits 90 which provide band pass filtering. The band limited instrumentation amplifier will be followed by more gain and a very steep high cut-off switched filter. The switched filter will feed a two stage high cut filter (used to remove and clock feed through from the switched filter) then to the sample and hold circuits 88. The outputs of the sample and hold circuits 88 are connected to an analog multiplexer 91 and 16 bit analog to digital converter 92. The recorded EEG will normally be digitised to 16 bit accuracy. A 16 bit dynamic range means that the analog front-end gain can be fixed at a predetermined value for typical patients. As the analog multiplexer 91 is fed by individual sample and hold circuits 88 (one per EEG channel) no data time skewing will occur. All EEG data and other relevant timing information will be stored in the hard drive 44. The computer then uploads this data to the central analysis site 4.

In order to maximise patient comfort, the brightness of the visual flicker is preferably slowly increased to its final value over a period of minutes.

Figure 12:
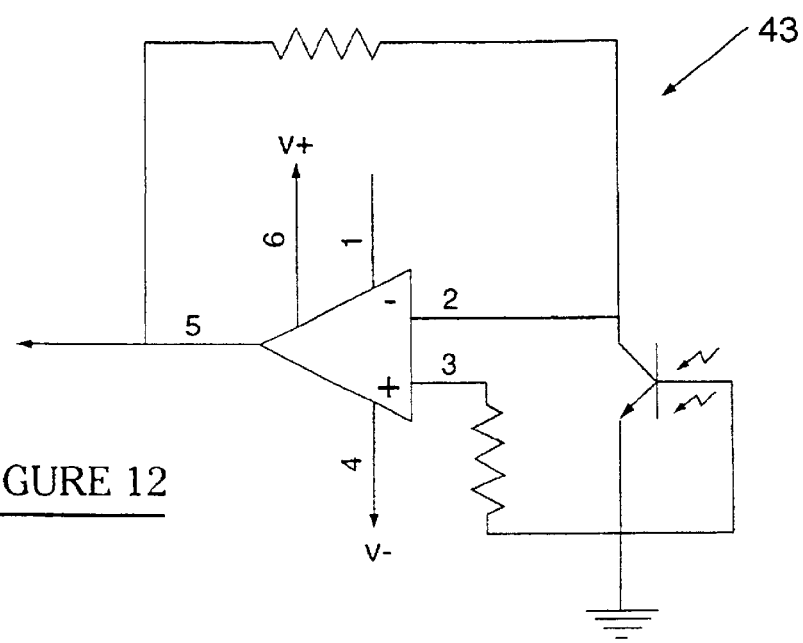
FIG. 12 shows a circuit for detecting ambient light levels.

The visor may include a light detector 48 for detecting ambient light levels, the detector 48 being coupled to an ambient light level detector circuit 43, an example of which is shown in FIG. 12. The circuit 43 converts the ambient light level to a voltage signal which is coupled by an amplifier, low pass filter 93, and sample and hold circuit 95 to the multiplexor 91, as shown in FIG. 4. Voltage signals from the phototransistor 43 pass through the convertor 92 and are inputted to the microprocessor 68. The voltage drive from the phototransistor 43 is linearly proportional to the ambient light brightness. This voltage will be measured by software in the microprocessor to give a brightness value. If the brightness value is too high, ambient light levels are too high and a message will be generated to advise the clinician to reduce the ambient light levels.

The microprocessor 68 also controls the acquisition of data by signalling the analog to digital converter 92 to measure the current EEG value at an electrode 82, as determined by the microprocessor. This data will be stored in the S-RAM 94. The microprocessor with the front-end amplifiers preferably include several high accuracy 32 bit counter/timers capture circuits 102. These 32 bit counter/timers capture circuits 102 generate the timing signals for data acquisition, visual flicker frequency as well as specific events in the material being presented to the patient. Such events may include the beginning and end of task sequences as well as the timing of specific events. The timing data held in counters 102 can be captured when signalled by the above mentioned events. The captured timing data can be stored along with the recorded EEG data in the hard drive 44 and for later transmission and analysis. Software at test site may also detect any possible development of photo-epilepsy by monitoring the amplitude of the EEG at the flicker stimulus frequency. In the event of any photo-epilepsy being detected, the flicker stimulus will be discontinued and the test terminated.

At the end of data acquisition, the data is encrypted and transferred to the central analysis site 4.

Cognitive tasks can be presented at the test site by using in-house software such as "PIPSCRIPT" or commercial software such as CANTAB or Ulead Media Studio. It will be appreciated by those skilled in the art that commercially available software packages can be utilised to perform the file storage and transfer functions required in carrying out the techniques of the invention. Standard Internet communication software such as WS FTP32 or Cute FTP can be used to download multimedia files. These files can be compressed and encrypted using software such as WINZIP. Transfer of encrypted brain activity data can be transferred to the central analysis site 4 via FTP.

The CPU 16 may comprise a Silicon Graphics workstation or WINTEL based system. A high security computer network fire-wall can be installed to reduce the risks of malicious hacking in accordance with known practice.

Preferably the material which constitutes the cognitive task as well as brain electrical activity is held in the storage device 26 for ongoing access. Also, archival storage may be provided and a very high capacity tape system (at least 10,000 gigabyte) is preferred. Archiving may be done using Digital Video Disk (DVD) media.

Software in the CPU 16 calculates Steady State Visually Evoked Potential (SSVEP) amplitude and phase for each stimulus cycle. The SSVEPC refers to the mean coherence over the entire duration of a cognitive task while the ER-SSVEPC refers to the changes in coherence over the duration of a typical trial in a cognitive task. Calculation accomplished used Fourier techniques using equations 1.0 and 1.1.

$$a_n = \frac{1}{S \Delta \tau} \sum_{i=0}^{S-1} f(nT + i\Delta\tau) \cos\left(\frac{2\pi}{T}(nT + i\Delta\tau)\right) \quad 1.0$$

$$b_n = \frac{1}{S \Delta \tau} \sum_{i=0}^{S-1} f(nT + i\Delta\tau) \sin\left(\frac{2\pi}{T}(nT + i\Delta\tau)\right)$$

Calculation of SSVEP Fourier components where $a_n$ and $b_n$ are the cosine and sine Fourier coefficients respectively. n represents the $n^{th}$ stimulus cycle, S is the number of samples per stimulus cycle (16), $\Delta\tau$ is the time interval between samples, T is the period of one cycle and $f(nT+i\Delta\tau)$ is the EEG signal.

$$SSVEP_{amplitude} = \sqrt{(a_n^2 + b_n^2)} \quad 1.1$$

$$SSVEP_{phase} = a\tan\left(\frac{b_n}{a_n}\right)$$

Calculation of SSVEP amplitude and phase where $a_n$ and $b_n$ are the cosine and sine Fourier coefficients respectively.

Amplitude and phase components can be calculated using either single cycle Fourier coefficients or coefficients that have been calculated by integrating across multiple cycles.

In addition to SSVEP amplitude and phase changes associated with the therapeutic intervention, it is also possible to determine the therapeutic intervention induced changes in the relationship between the SSVEP at different electrodes by measuring the coherence. The coherence is similar to the correlation coefficient expressed as a function of frequency.

Two types of coherence functions are calculated from the SSVEP sine and cosine Fourier coefficients while patients undertake the cognitive task. One will be termed the SSVEP Coherence (SSVEPC) and the other, Event Related SSYEP Coherence (ER-SSVEPC).

SSVEPC

The SSVEP sine and cosine coefficients can be expressed as complex numbers $$C_n = (a_n, b_n) \qquad 1.2$$

where $a_n$ and $b_n$ have been previously defined.

The nomenclature is generalised to take into account multiple tasks and multiple electrodes.

$$C_{g,e,n} = (a_{g,e,n}, b_{g,e,n}) \qquad 1.3$$

where g=the task number
e=the electrode
n=the point in time

Relevant functions can be defined by the following equations:

$$\gamma_{g,e1,e2} = H_{g,e1,e2} / T_{g,e1,e2} \qquad 1.4$$

$$H_{g,e1,e2} = \sum_{n=1}^{n=T} C_{g,e1,n} \cdot C'_{g,e2,n} \qquad 1.5$$

and $$T_{g,e1,e2} = \sqrt{\left(\sum_{n=1}^{T} C_{g,e1,n} \cdot C'_{g,e1,n}\right)\left(\sum_{n=1}^{T} C_{g,e2,n} \cdot C'_{g,e2,n}\right)} \qquad 1.6$$

The SSVEPC coherence is then given by $$\gamma^2_{g,e1,e2} = |H_{g,e1,e2}|^2 / T^2_{g,e1,e2} \qquad 1.7$$

And the phase of the SSVEPC is given by $$\Phi_{g,e1,e2} = \operatorname{Tan}^{-1}\left(\frac{\operatorname{Im}(H_{g,e1,e2})}{\operatorname{Re}(H_{g,e1,e2})}\right) \qquad 1.8$$

ERSSVEP-C

In this case, the coherence across trials in a particular task are calculated. This yields coherence as a function of time. We generalise the nomenclature to take into account multiple tasks and multiple electrodes.

$$C_{g,d,e,n} = (a_{g,d,e,n}, b_{g,d,e,n}) \qquad 1.9$$

where g=the task number
d=the trial within a particular task, e.g. a specific response
e=the electrode
n=the point in time Relevant functions can be defined by the following equations:

$$\gamma_{g,e1,e2,n} = H_{g,e1,e2,n} / T_{g,e1,e2,n} \qquad 1.10$$

$$H_{g,e1,e2,n} = \sum_{d=1}^{d=D} C_{g,e1,d,n} \cdot C'_{g,e2,d,n} \qquad 1.11$$

and $$T_{g,e1,e2,n} = \sqrt{\left(\sum_{d=1}^{D} C_{g,e1,d,n} \cdot C'_{g,e1,d,n}\right)\left(\sum_{d=1}^{D} C_{g,e2,d,n} \cdot C'_{g,e2,d,n}\right)} \qquad 1.12$$

The SSVEPC is then given by $$\gamma^2_{g,e1,e2,n} = |H_{g,e1,e2,n}|^2 / T^2_{g,e1,e2,n} \qquad 1.13$$

And the phase of the SSVEPC is given by $$\Phi_{g,e1,e2,n} = \operatorname{Tan}^{-1}\left(\frac{\operatorname{Im}(H_{g,e1,e2,n})}{\operatorname{Re}(H_{g,e1,e2,n})}\right) \qquad 1.14$$

The step of assessing the efficacy includes the steps of detecting changes associated with therapeutic intervention in the SSVEP amplitude and/or phase topography.

Precise timing on the various events is supplied by the encrypted data file uploaded from patients.

Information about brain activity and brain speed of processing is preferably available for each of the recording sites. Preferably there are about sixty-four scalp recording sites.

The CPU 16 may also run software for producing written reports outlining the response of the patient's brain to the test therapeutical treatment. The clinician administering the test treatment can then decide on the suitability of continued administration of the therapeutical treatment for the particular patient.

In summary, SSPT is to be used to evaluate therapeutic intervention in patients suffering from a wide range of neuropsychiatric disorders including, but not limited to, disorders of mood, anxiety disorders, neurodegenerative disorders (e.g. Alzheimer's dementia), disorders of attention, cognition and impulse control. Patients will be required to perform a number of specified cognitive tasks before and after therapeutic intervention. The steady state visually evoked potential (SSVEP) will be recorded from (typically) 64 scalp sites while patients undertake the cognitive tasks.

Changes in the SSVEP amplitude and phase topography are used to ascertain the effectiveness of the therapeutic intervention. For example, the short term (2 hours) response to a dose of psychotropic medication (eg a neurostimulant or an antidepressant) may be used to predict the long term responsiveness to such medication. The clinician may then use the SSPT technology to select the most effective medication regimen (such as selection of drug, dosage and optimum treatment duration).

EXAMPLE 1

An example of the invention will now be briefly described with reference to FIGS. 15 and 16. The method was used on patients who are children diagnosed with Attention Deficit Hypoactivity Disorder (ADHD).

Children diagnosed with ADHD were tested to examine the effects of stimulant medication (methylphenidate or Ritalin) on the amplitude and phase of the steady state visually evoked potential (SSVEP). The children performed two cognitive tasks before the stimulant medication was administered and then repeat the tasks one hour after stimulant medication was administered.

The first task was a low demand vigilance task where the patients were required to press a micro switch on the predictable appearance of the number "5" in the repeated sequence "1, 2, 3, 4, 5". The second task was known as the A-X version of the Continuous Performance Task (CPT A-X). In this more demanding task, patients were required to press a micro switch on the appearance of the letter "X" if and only if it has been preceded by the letter "A".

Figure 15:
FIGS. 15 and 16 show typical changes in SSVEP in response to medication.
Figure 16:
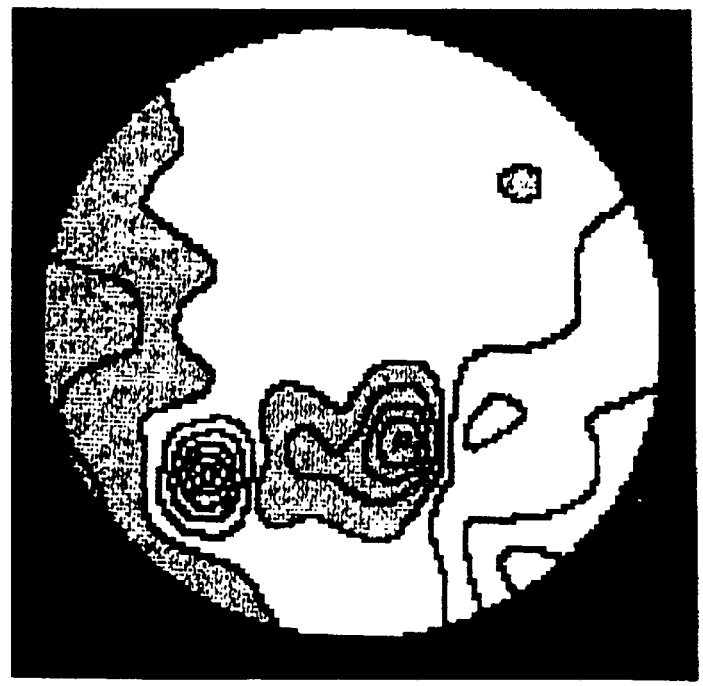

FIGS. 15 and 16 illustrate the spatial distribution of the difference between the mean SSVEP phase, evaluated over the entire CPT A-X task before medication, and the point in time corresponding to the disappearance of the letter "A" in the CPT A-X task after medication.

More particularly, FIG. 15 shows changes in SSVEP phase during the performance of the Continuous Performance Task in a 12 year old boy diagnosed with ADHD and responding to the stimulant medication. Scalp distribution of SSVEP latency is viewed from the top of the head. The uppermost portion of map illustrates activity in frontal brain sites while the bottom corresponds to the back (occipital lobe) of the head. Light areas are associated with SSVEP phase advance (latency reduction), grey areas illustrate regions of SSVEP latency increase. Contours correspond to latency changes of 6 msec. The presence of large SSVEP latency reduction at prefrontal sites predicts a good long term clinical response to the stimulant medication for the patient.

In contrast, FIG. 16 shows changes in SSVEP phase during the performance of the Continuous Performance Task in a different 12 year old boy diagnosed with ADHD and not responding to stimulant medication. The absence of SSVEP latency reduction at prefrontal sites predicts a poor long term clinical response to the stimulant medication for the patient.

In summary, the spatial distribution shown in FIG. 15 shows a strong reduction in the SSVEP latency at prefrontal scalp sites which suggests a normalisation of brain activity during this task. It is suggested that such a response is indicative of a positive long-term response to stimulant medication. By contrast, the spatial distribution illustrated in FIG. 16 shows little or no latency reduction at prefrontal sites. This result suggests that there would be a poor response in that patient to stimulant medication.

Many modifications will be apparent to those skilled in the art without departing from the spirit and scope of the invention.

What is claimed is:

1. A method of evaluating the efficacy of treatment of a neuropsychiatric disorder of a patient at a remote site comprising the steps of:

presenting a first cognitive task to the patient at the remote site;

recording a first steady state visually evoked potential (SSVEP) corresponding to when the patient is presented with the first cognitive task;

administering a dose of psychotropic medication to the patient;

presenting a second cognitive task to the patient at the remote site, the second cognitive task being similar to or the same as the first cognitive task;

recording a second steady state visually evoked potential (SSVEP) corresponding to when the patient is presented with the second cognitive task; and assessing at a central site the efficacy of the psychotropic medication on the basis of differences between the first and second SSVEPs.

2. A method as claimed in claim 1 wherein the step of assessing the efficacy comprises the step of detecting changes in coherence of said first and second SSVEPs.

3. A method as claimed in claim 1 comprising the steps of obtaining first output signals representing the response of the patient's brain to said first cognitive task;

obtaining second output signals representing the response of the patient's brain to said second cognitive task whilst under the influence of said medication;

transmitting the first and second output signals to the central site; and calculating the amplitude, phase and/or coherence of said first and second SSVEPs from said first and second signals respectively.

4. A method as claimed in claim 3 comprising the steps of transmitting from the central site to the remote site first and second input signals representative of said first and second cognitive tasks.

5. A method as claimed in claim 4 wherein the first and second input signals and the first and second output signals are transmitted via the Internet.

6. A method as claimed in claim 5 wherein there are a plurality of said remote sites.

7. A method as claimed in claim 5 wherein a report of the step of assessing the efficacy is transmitted to a clinician at the remote site.

8. A method as claimed in claim 1 wherein a clinician administers the dose of psychotropic medication to the patient at the remote site and a report on the step of assessing the efficacy of the psychotropic medication is transmitted to the clinician via the Internet.

9. A method as claimed in claim 8 wherein the dose is a test dose and said report comprises an indication whether or not the patient is likely to benefit from long term administration of the psychotropic medication.

10. A method as claimed in claim 8 wherein the first and second cognitive tasks are download from the Internet at the remote site.

11. A method as claimed in claim 1 wherein the psychotropic medication comprises a chemical compound or compounds used in the treatment of psychiatric, psychological, behavioural, educational or neurological disorders.

12. A method as claimed in claim 1 wherein the step of assessing the efficacy comprises the step of detecting changes in amplitude and/or phase of said first and second SSVEPs.

13. A method as claimed in claim 3 wherein the steps of obtaining first and second output signals are effected by placing electrodes on the scalp of the patient, the first and second output signals being produced on said electrodes and the step of assessing the efficacy comprises detecting changes in inter-electrode SSVEP coherence.

* * * * *